(12) United States Patent
Bulinski et al.

(10) Patent No.: US 9,540,316 B2
(45) Date of Patent: Jan. 10, 2017

(54) NITROGEN CONTAINING HYDROFLUOROETHERS AND METHODS OF MAKING SAME

(71) Applicant: 3M INNOVATIVE PROPERTIES COMPANY, St. Paul, MN (US)

(72) Inventors: Michael J. Bulinski, Stillwater, MN (US); Michael G. Costello, Afton, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 14/904,446

(22) PCT Filed: Jul. 21, 2014

(86) PCT No.: PCT/US2014/047349
§ 371 (c)(1),
(2) Date: Jan. 12, 2016

(87) PCT Pub. No.: WO2015/013155
PCT Pub. Date: Jan. 29, 2015

(65) Prior Publication Data
US 2016/0145195 A1    May 26, 2016

Related U.S. Application Data

(60) Provisional application No. 61/858,202, filed on Jul. 25, 2013.

(51) Int. Cl.
| | | |
|---|---|---|
| *C07C 217/46* | (2006.01) | |
| *C07D 207/10* | (2006.01) | |
| *C07D 211/38* | (2006.01) | |
| *C11D 7/50* | (2006.01) | |
| *C07D 223/04* | (2006.01) | |
| *C07D 241/04* | (2006.01) | |
| *C07D 265/30* | (2006.01) | |
| *C07D 279/12* | (2006.01) | |
| *C11D 1/00* | (2006.01) | |
| *C09K 5/00* | (2006.01) | |

(52) U.S. Cl.
CPC .......... *C07C 217/46* (2013.01); *C07D 207/10* (2013.01); *C07D 211/38* (2013.01); *C07D 223/04* (2013.01); *C07D 241/04* (2013.01); *C07D 265/30* (2013.01); *C07D 279/12* (2013.01); *C09K 5/00* (2013.01); *C11D 1/004* (2013.01); *C11D 7/5018* (2013.01)

(58) Field of Classification Search
CPC ... C07C 217/46; C07D 223/04; C07D 241/04; C07D 265/30; C07D 279/12; C07D 211/38; C07D 207/10; C11D 1/004; C11D 7/5018; C09K 5/00

USPC ................................ 564/508; 544/177, 398
See application file for complete search history.

(56) References Cited

U.S. PATENT DOCUMENTS

| | | | |
|---|---|---|---|
| 2,713,593 | A | 7/1955 | Brice |
| 3,903,012 | A | 9/1975 | Brandreth |
| 4,169,807 | A | 10/1979 | Zuber |
| 5,125,089 | A | 6/1992 | McCambridge |
| 5,925,611 | A | 7/1999 | Flynn |
| 6,080,448 | A | 6/2000 | Leiner |
| RE37,119 | E | 4/2001 | Sherwood |
| 6,374,907 | B1 | 4/2002 | Tousignant |
| 8,418,530 | B1 | 4/2013 | Scaringe |
| 2007/0267464 | A1 | 11/2007 | Vitcak |
| 2011/0100601 | A1 | 5/2011 | Flynn |

FOREIGN PATENT DOCUMENTS

| | | |
|---|---|---|
| WO | WO 02-40102 | 5/2002 |
| WO | WO 2010-094019 | 8/2010 |

OTHER PUBLICATIONS

Banks, Preparation, Properties and Industrial Applications of Organofluorine Compounds, 19-43 (1982).
Kurykin, "Reaction of trans-perfluoro-2-pentene with alcoholates", Academy of Sciences of the USSR, Division of chemical science, 1981, vol. 30, No. 11, pp. 2203-2206.
International Search Report for PCT International Application No. PCT/US2014/47349, mailed on Oct. 24, 2014, 4pgs.

*Primary Examiner* — Jafar Parsa
(74) *Attorney, Agent, or Firm* — Adam Bramwell

(57) ABSTRACT

Provided are amine-containing hydrofluoroether compounds represented by the following general formula (I), wherein (I) Y is a single bond or CF2 and wherein (i) Rf.1 and Rf2 are independently linear or branched perfluoroalkyl groups having with 1-8 carbon atoms and optionally comprise at least one catenated heteroatom, or (ii) Rf1 and Rf2 are bonded together to form a ring structure having 4-6 carbon atoms and optionally comprise one or more catenated heteroatoms; with the proviso that if Rf1 and Rf2 are bonded together to form a ring structure comprising a nitrogen heteroatom, said nitrogen heteroatom is tertiary and is bonded to a perfluoroalkyl group having 1-3 carbon atoms.

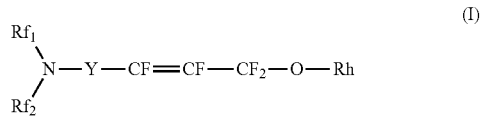

(I)

9 Claims, No Drawings

NITROGEN CONTAINING HYDROFLUOROETHERS AND METHODS OF MAKING SAME

CROSS REFERENCE TO RELATED APPLICATIONS

This application is a national stage filing under 35 U.S.C. 371 of PCT/US2014/047349, filed Jul. 21, 2014, which claims priority to U.S. Application No. 61/858,202, filed Jul. 25, 2013, the disclosure of which is incorporated by reference in its/their entirety herein.

CROSS REFERENCE TO RELATED APPLICATIONS

This application claims priority to U.S. Provisional Patent Application No. 61/858,202, filed Jul. 25, 2013, the disclosure of which is incorporated by reference in its entirety herein.

FIELD

The present disclosure relates to hydrofluoroether compounds and methods of making and using the same. More specifically, the present disclosure relates to olefin-type hydrofluoroether compounds containing nitrogen atoms, and methods of making and using the same.

BACKGROUND

Various hydrofluoroether compounds are described, for example, in WO 2010094019 (Bartelt et al.), and Reaction of Trans-perfluoropent-2-ene with alcoholates, Kurykin, M. A., German, L. S. Izvestiya Akademii Nauk SSSR, Seriya Khimicheskaya (1981), (11), 2647-50.

SUMMARY

In some embodiments, a hydrofluoroether compound represented by the following general formula (I) is provided.

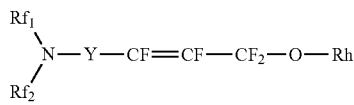

(I)

$Rf_1$ and $Rf_2$ are independently linear or branched perfluoroalkyl groups having with 1-8 carbon atoms and optionally comprise at least one catenated heteroatom, or $Rf_1$ and $Rf_2$ are bonded together to form a ring structure having 4-6 carbon atoms and optionally comprise one or more catenated heteroatoms. Y is $CF_2$ or a single bond. Rh is a linear or a branched alkyl group having with 1-3 carbon atoms and optionally comprises at least one catenated heteroatom. If $Rf_1$ and $Rf_2$ are bonded together to form a ring structure comprising a nitrogen heteroatom, said nitrogen heteroatom is tertiary and is bonded to a perfluoroalkyl group having 1-3 carbon atoms.

In some embodiments, a process for transferring heat is provided. The process includes transferring heat between a heat source and a heat sink through the use of a heat transfer agent comprising a hydrofluoroether compound as described above.

In some embodiments, a process for depositing a coating on a substrate is provided. The process includes applying to at least a portion of at least one surface of said substrate a composition that include (a) a solvent composition that includes a hydrofluoroether compound as described above; and (b) at least one coating material that is soluble or dispersible in said solvent composition.

In some embodiments, a process for removing a contaminant from an article is provided. The process includes contacting the article with a hydrofluoroether compound as described above. The contaminants may include, for example, oils, greases, particulates, water, and other known contaminants.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

Hydrofluoroether compounds (HFEs) comprise a class of commercially valuable chemical compounds. The term hydrofluoroether, as used in the art, commonly refers to those ethers having partial substitution of hydrogen atoms by fluorine atoms. Some hydrofluoroethers are commercially available. Examples include those hydrofluoroethers available under the trade designations 3M Novec™ Engineered Fluid 7000, 7100, 7200, 7300, 7500, and 7600 from 3M Company of Saint Paul, Minn. Hydrofluoroethers have been used in applications such as cleaning solvents, deposition solvents, battery electrolyte solvents, and heat transfer media. The uses of hydrofluoroethers can be limited by their thermal stability.

In view of an increasing demand for environmentally friendly chemical compounds, it has been recognized that there exists an ongoing need for new HFEs exhibiting further reductions in environmental impact, and which can meet the performance requirements of a variety of different applications, and be manufactured cost-effectively.

DEFINITIONS

As used herein, "catenated heteroatom" means an atom other than carbon (for example, oxygen, nitrogen, or sulfur) that is bonded to carbon atoms in a carbon chain so as to form a carbon-heteroatom-carbon chain.

As used herein, "fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, "substituted" (in reference to a group or moiety) means that at least one carbon-bonded hydrogen atom is replaced with an alkyl, fluoroalkyl, or perfluoroalkyl group that optionally contains one or more catenated heteroatoms.

As used herein "CF=CF" includes cis isomers, trans isomers, and combinations thereof.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to compounds represented by the following general formula (I):

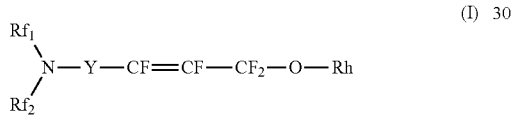

In illustrative embodiments, $Rf_1$ and $Rf_2$ may be independently linear or branched perfluoroalkyl groups having 1-8 carbon atoms, 2-6 carbon atoms, or 2-4 carbon atoms. In further embodiments, $Rf_1$ and $Rf_2$ may be bonded together to form ring structure having 4-6 carbon atoms, 4-5 carbon atoms, or 4 carbon atoms. Optionally, $Rf_1$ and $Rf_2$ may include one or more catenated heteroatoms. In some embodiments, Y may be $CF_2$ or a single bond.

In various embodiments, Rh may be a linear or a branched alkyl group having with 1-3 carbon atoms or 1-2 carbon atoms. Optionally, Rh may include one or more catenated heteroatoms.

In some embodiments, if $Rf_1$ and $Rf_2$ are bonded together to form a ring structure that includes a nitrogen heteroatom, the nitrogen heteroatom may be tertiary, and may be bonded to a perfluoroalkyl group having 1-3 carbon atoms or 1-2 carbon atoms.

Representative examples of the hydrofluoroether compounds of the present disclosure may include the following:

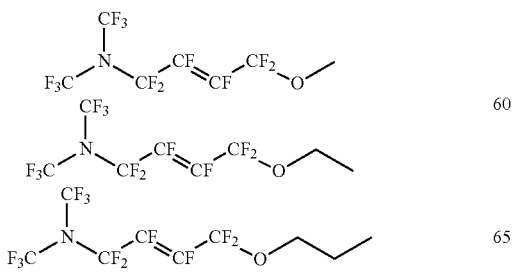

-continued

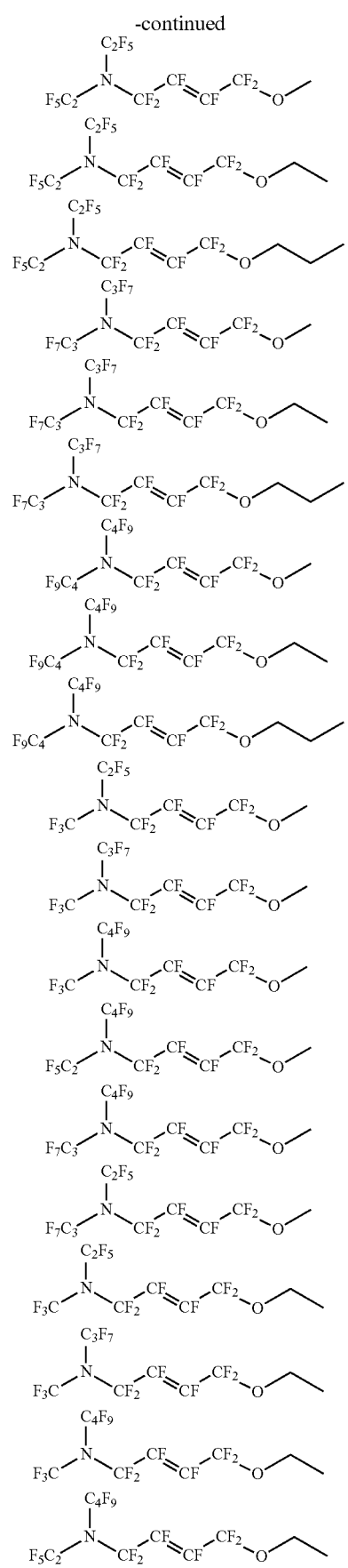

-continued
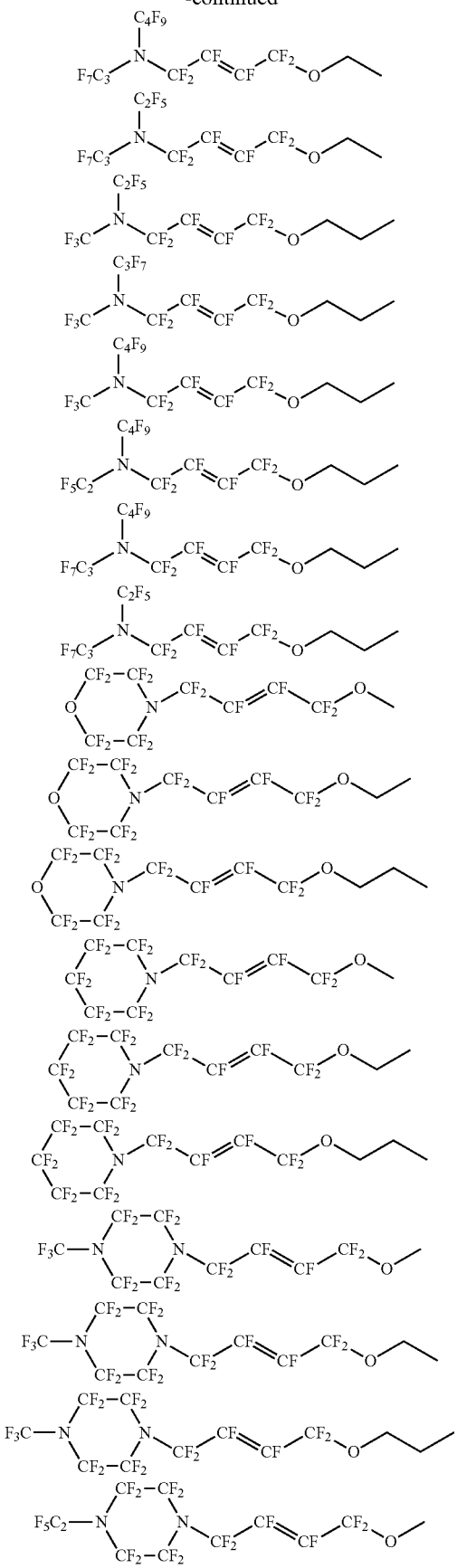
-continued
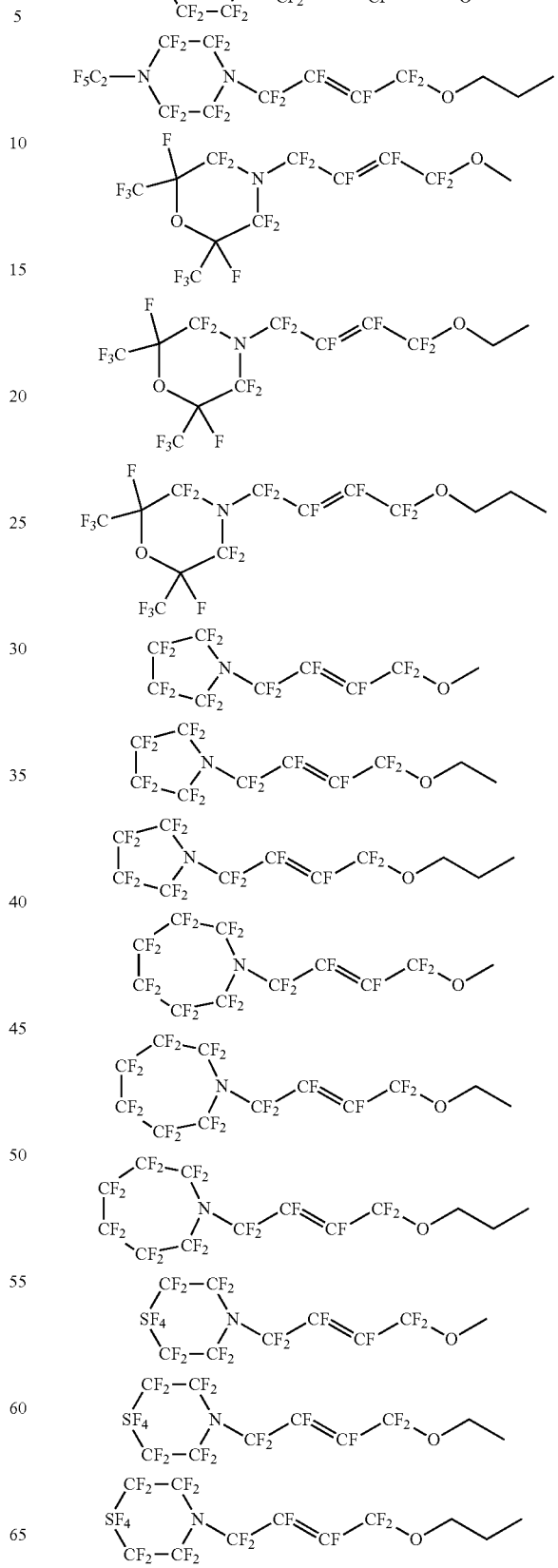

-continued
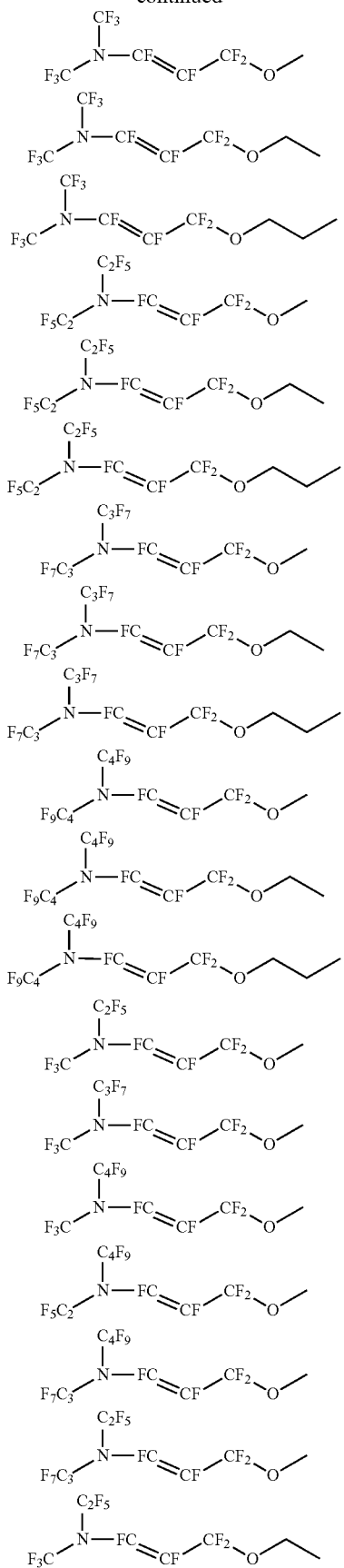
-continued
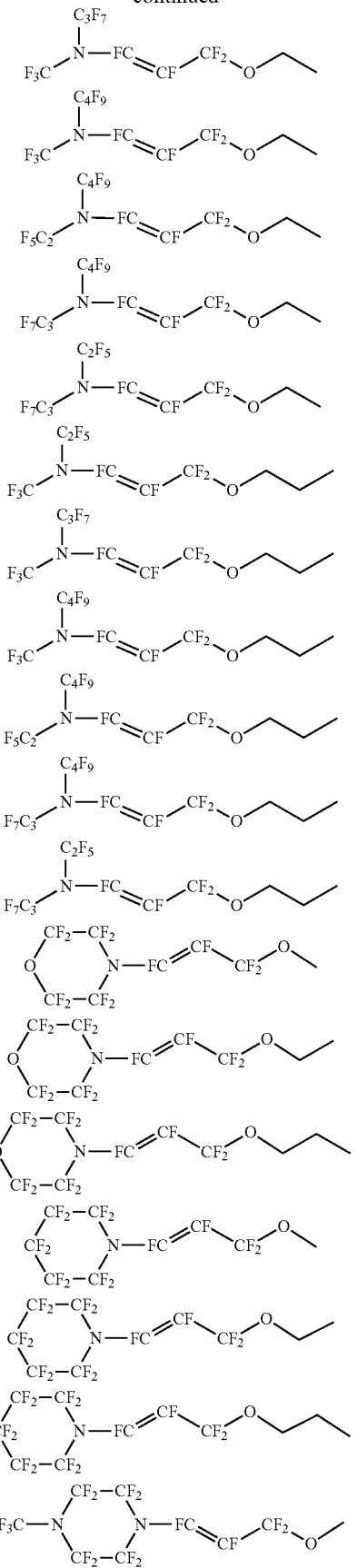

-continued

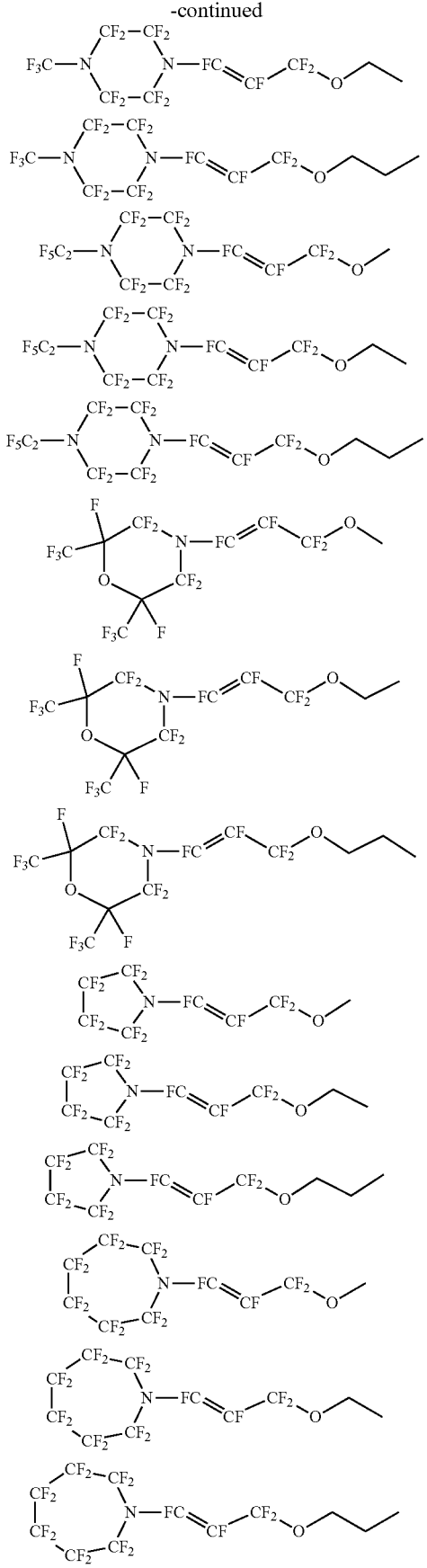

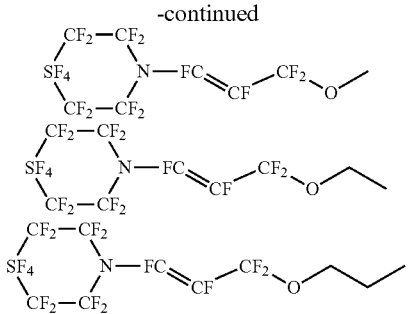

In some embodiments, the hydrofluoroether compounds of the present disclosure may be hydrophobic, relatively chemically unreactive, thermally stable, water insoluble, and normally liquid (for example, at 20° C.) Additionally, the hydrofluoroether compounds of the present disclosure may have a low environmental impact relative to known hydrofluoroether compounds. In this regard, the hydrofluoroether compounds of the present disclosure may have a global warming potential (GWP) of less than 10, less than 5, or even less than 2. As used herein, GWP is a relative measure of the warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{0i} e^{-t/\tau} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In illustrative embodiments, the hydrofluoroether compounds of the present disclosure (or compositions comprising, consisting, or consisting essentially thereof) can be used in various applications where CFCs, known HFEs, and perfluorcarbons have been used. For example, the compounds can be used as solvents for precision or metal cleaning of electronic articles such as disks or circuit boards; as heat transfer agents; as cell size regulators in making foam insulation (for example, polyurethane, phenolic, and thermoplastic foams); as chemical fire extinguishing agents in streaming applications; as carrier fluids or solvents for document preservation materials and for lubricants; as power cycle working fluids such as for heat pumps; as inert media for polymerization reactions; as buffing abrasive agents to remove buffing abrasive compounds from polished surfaces such as metal; as displacement drying agents for removing water, such as from jewelry or metal parts; as resist developers in conventional circuit manufacturing techniques including chlorine-type developing agents; and as strippers for photoresists.

In some embodiments, the hydrofluoroether compounds can be used alone or in admixture with each other or with other commonly-used solvents (for example, alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, and the like, and mixtures thereof). Such co-solvents can be chosen to modify or enhance the properties of a composition for a particular use and can be utilized in ratios (of co-solvent(s) to hydrofluoroether(s)) such that the resulting composition preferably has no flash point.

In various embodiments, minor amounts of optional components can be added to the compounds to impart particular desired properties for particular uses. Useful compositions can comprise conventional additives such as, for example, surfactants, coloring agents, stabilizers, anti-oxidants, flame retardants, and the like, and mixtures thereof.

In illustrative embodiments, the hydrofluoroether compounds can be useful as solvents for cleaning and drying applications such as, for example, those described in U.S. Pat. No. 5,125,089 (Flynn et al.), U.S. Pat. No. 3,903,012 (Brandreth), U.S. Pat. No. 4,169,807 (Zuber), and U.S. Pat. No. 5,925,611 (Flynn et al.), the descriptions of which are incorporated by reference herein. Both organic and inorganic substrates can be cleaned by contacting them with a composition comprising an HFE of the present disclosure. Contaminants that can be removed include, for example, hydrocarbon contaminants, fluorocarbon contaminants, particulates, and water.

In some embodiments, the hydrofluoroether compounds can be useful as heat transfer agents, such as that described in, for example, U.S. Reissue Pat. No. 37,119 E (Sherwood) and U.S. Pat. No. 6,374,907 B1 (Tousignant et al.), which descriptions are incorporated by reference herein. In carrying out such processes, heat is transferred between a heat source (for example, a silicon wafer or a component of a flat panel display) and a heat sink through the use of a heat transfer agent comprising a hydrofluoroether compound of the present disclosure. The HFEs generally exhibit a wide liquid range, useful viscosity over that range, and relatively high thermal stability at end use temperatures, making them well-suited for use as heat transfer fluids.

In using the hydrofluoroether compounds of the disclosure as deposition solvents in coating applications or in document preservation applications, the processes described in, for example, U.S. Pat. No. 5,925,611 (Flynn et al.) and U.S. Pat. No. 6,080,448 (Leiner et al.) can be used, which descriptions are incorporated by reference herein. Such processes for depositing a coating on a substrate (for example, magnetic recording media or cellulose-based materials) comprises applying, to at least a portion of at least one surface of the substrate, a composition comprising (a) a solvent composition comprising a hydrofluoroether compound of the present disclosure; and (b) at least one coating material that is soluble or dispersible in the solvent composition. Coating materials that can be deposited by the process include, for example, pigments, lubricants, stabilizers, adhesives, anti-oxidants, dyes, polymers, pharmaceuticals, release agents, inorganic oxides, document preservation materials (for example, alkaline materials used in the deacidification of paper), and the like, and combinations thereof. Materials further include perfluoropolyether, hydrocarbon, and silicone lubricants; amorphous copolymers of tetrafluoroethylene; polytetrafluoroethylene; document preservation materials; and combinations thereof.

In some embodiments, the hydrofluoroether compounds of the present disclosure can be prepared by electrochemically fluorinating a dimethyl ester to produce the perfluorinated di-acyl fluoride. The dimethyl esters can be prepared by well known methods in the literature such as the Michael reaction of an amine with an alkene such as dimethyl maleate or dimethyl itaconate. Once prepared these organics can be made to undergo electrochemical fluorination by the method described in, for example, U.S. Pat. No. 2,713,593 (Brice et al.) and in R. E. Banks, Preparation, Properties and Industrial Applications of Organofluorine Compounds, pages 19-43, Halsted Press, New York (1982)). Upon isolation, these difunctional acid fluorides can be reacted with alkylating reagents such as dimethyl sulfate or diethyl sulfate selectively to produce the intermediate hydrofluoroether acyl fluoride. This intermediate can then undergo a decarboxylation reaction to product the hydrofluoroether compounds of the present disclosure.

The operation of the present disclosure will be further described with regard to the following detailed examples. These examples are offered to further illustrate the various specific and preferred embodiments and techniques. It should be understood, however, that many variations and modifications may be made while remaining within the scope of the present disclosure.

EXAMPLES

Example 1

Preparation of 2,2,3,3,5,5,6,6-octafluoro-4-(1,2,3,3-tetrafluoro-3-methoxy-prop-1-enyl)morpholine

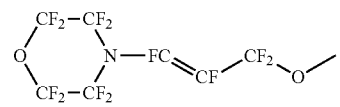

In a 2 L 3-neck round bottom flask equipped with overhead stirring, thermocouple, heating mantle, cold water condensor and a dry N2 bubbler, 2,2,3-trifluoro-3-(2,2,3,3,5,5,6,6-octafluoromorpholin-4-yl)butanedioyl difluoride (331 g 0.81 mol) (prepared via electrochemical fluorination of dimethyl 2-morpholinobutanedioate via a Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)) was combined with dimethyl sulfate (102 g 0.81 mol, Sigma-Aldrich), potassium fluoride (47 g 0.81 mol, Sigma-Aldrich), adogen (22 g, Sigma Aldrich), and diglyme (400 g, Sigma-Aldrich). The reaction mixture was stirred at a temperature of 32° C. for 16 hours. 200 mL of water was added slowly then to the mixture and once the exotherm subsided the reaction was heated to 65° C. for 1 hour. After heating for 1 hour a Dean-Stark distillation apparatus was inserted into the reflux line and the crude fluorochemical product was steam distilled. A total of 282 g of product was collected which was dried over anhydrous magnesium sulfate and then filtered. The product was then fractionally distilled (b.p.=130° C.). The product structure as a mixture of cis and trans isomers was verified by GC/MS and F-19 and H-1 NMR.

Example 2

Preparation of 1,1,2,3,4,4-hexafluoro-4-methoxy-N,N-bis(trifluoromethyl)but-2-en-1-amine

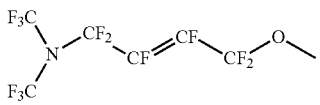

In a 2 L 3-neck round bottom flask equipped with overhead stirring, thermocouple, heating mantle, cold water condensor and dry N2 line, 2-[[bis(trifluoromethyl)amino]-difluoro-methyl]-2,3,3-trifluoro-butanedioyl difluoride (300 g, 0.7 mol) (prepared via electrochemical fluorination of dimethyl 2-(dimethylaminomethyl)butanedioate via a Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)) was combined with dimethyl sulfate (99.0 g 0.8 mol, Sigma-Aldrich), potassium fluoride (45.6 g 0.8 mol, Sigma-Aldrich), diglyme solvent (600 g, Sigma-Aldrich) and Adogen phase transfer catalyst (20.8 g, Sigma-Aldrich). The mix was heated to 32° C. for 24 hours. After the hold 500 g of PF-5060 (perfluorohexane available from 3M Company) was added to extract the product. The fluorocarbon phase was then separated and filtered. An analysis of this phase by GC-FID showed that it is substantially the desired product. This intermediate product was fractionally distilled to remove the extractant and isolate the product. 50 g of the intermediate, 2-[[bis(trifluoromethyl)amino]-difluoro-methyl]-2,3,3,4,4-pentafluoro-4-methoxy-butanoyl fluoride was combined with anhydrous sodium carbonate (15.4 g 0.15 mol, Sigma-Aldrich) and 100 mL of diglyme as solvent. The reaction mixture was gradually heated to 130° C. over several hours. During this time evolution of $CO_2$ was observed indicating the decarboxylation reaction was taking place. The product was distilled from the reaction mixture. The crude fluorochemical material that was collected was purified by fractional distillation. The product boiling point is 103° C. The product structure as a mixture of cis and trans isomers was confirmed by GC/MS and F-19 and H-1 NMR.

Example 3

Preparation of 2,2,3,3,4,4,5,5-octafluoro-1-(1,2,3,3-tetrafluoro-3-methoxy-prop-1-enyl)pyrrolidine

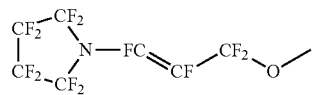

In a 2 1 3-neck round bottom flask fitted with overhead stirring, cold water condenser, dry nitrogen bubbler, heating mantle and thermocouple, 2,2,3-trifluoro-3-(2,2,3,3,4,4,5,5-octafluoropyrrolidin-1-yl)butanedioyl difluoride (178 g, 0.46 mol) (prepared via electrochemical fluorination of dimethyl 2-pyrrolidin-1-ylbutanedioate via a Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)) was combined with dimethyl sulfate (57.7 g 0.48 mol, Sigma-Aldrich), potassium fluoride (27.9 g 0.48 mol, Sigma-Aldrich), Adogen 464 (6.37 g, 0.014 mol, Sigma-Aldrich) and diglyme (400 g, Sigma-Aldrich). The mix was heated to 32° C. for 48 hours, after which 300 mL of water was added slowly to the reaction mixture to quench the dimethyl sulfate and to start the decarboxylation reaction. After the water addition was complete the mix was heated to 65° C. for two hours. A Dean-Stark trap was then inserted into the reflux line and the fluorochemical was distilled overhead. About 153 g of material was collected. This material was fractionally distilled using an Oldershaw column with automatic reflux control. The boiling point of the pure material is approximately 121° C. The product structure as a mixture of cis and trans isomers was confirmed by GC/MS.

Example 4

Preparation of 2,2,3,3,5,5,6,6-octafluoro-4-(1,1,2,3,4,4-hexafluoro-4-methoxy-but-2-enyl)morpholine

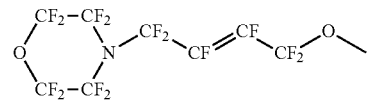

In a 5 L 3-neck round bottom flask fitted with overhead stirring, cold water condenser, dry nitrogen bubbler, heating mantle and thermocouple, 2-[difluoro-(2,2,3,3,5,5,6,6-octafluoromorpholin-4-yl)methyl]-2,3,3-trifluoro-butanedioyl difluoride (751 g 1.65 mol) (prepared via electrochemical fluorination of dimethyl 2-(morpholinomethyl)butanedioate via a Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)) was combined with dimethyl sulfate (208.15 g 1.65 mol, Sigma-Aldrich), potassium fluoride (100.66 g 1.73 mol, Sigma-Aldrich), Adogen 464 (22.97 g, 0.05 mol, Sigma-Aldrich) and diglyme (800 g, Sigma-Aldrich). The mix was heated to 32° C. for 24 hours, after which 300 mL of water was added slowly to the reaction mixture to quench the dimethyl sulfate and to start the decarboxylation reaction. A Dean-Stark trap was then inserted into the reflux line and the fluorochemical was distilled overhead. The fluorochemical that was recovered was purified by fractional distillation using an Oldershaw column with automatic reflux control. The pure material boiled at a temperature of 147° C. The product structure as a mixture of cis and trans isomers was verified by GC/MS.

Example 5

Preparation of 2,2,3,3,4,4,5,5,6,6-decafluoro-1-[(1,1,2,3,4,4-hexafluoro-4-methoxy-but-2-enyl]piperidine

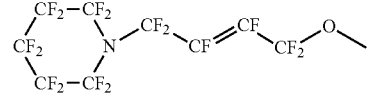

2-[(2,2,3,3,4,4,5,5,6,6-decafluoro-1-piperidyl)-difluoromethyl]-2,3,3-trifluoro-butanedioyl difluoride (323 grams, 0.66 moles), (prepared via electrochemical fluorination of dimethyl 2-(1-piperidylmethyl)butanedioate via Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)), potassium fluoride (74.0 grams, 1.27 moles), diglyme (747 grams) and Adogen 464 (15.5 grams, 0.03 moles) were combined in 3 liter 3-neck round bottom flask equipped with overhead stirring, cold water condenser, dry nitrogen bubbler, heating mantle and thermocouple. An exothermic reaction increased the temperature to 40° C. When the temperature decreased to 25° C., dimethyl sulfate (147 grams, 1.15 moles) was added to the flask and the contents were heated to 32° C. and held 18 hours. 500 mL of water and 105 grams of 50% potassium hydroxide were slowly added to the reaction mixture to quench the dimethyl sulfate and to start the decarboxylation reaction. The flask was heated to 65° C. and held two hours and then the mixture was distilled. The lower fluorochemical phase of the resulting distillate was then separated from the upper phase and washed once with water to afford 255 grams of material. This material was purified by fractional distillation using a vacuum jacketed Oldersahw column to give 96.2 grams product (boiling range 157-163° C.), purity >85% by gas-liquid chromatography). The product identity as a mixture of cis and trans isomers was confirmed by GCMS.

Example 6

Preparation of 2,2,3,3,5,5,6,6-octafluoro-1-[(E)-1,2,3,3-tetrafluoro-3-methoxy-prop-1-enyl]-4-(trifluoromethyl)piperazine

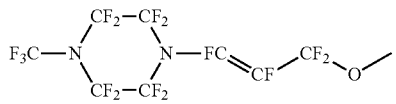

2,2,3-trifluoro-3-[2,2,3,3,5,5,6,6-octafluoro-4-(trifluoromethyl)piperazin-1-yl]butanedioyl difluoride (366 grams, 0.77 moles), (prepared via electrochemical fluorination of dimethyl 2-(4-methylpiperazin-1-yl)butanedioate via Simons ECF cell of essentially the type described in U.S. Pat. No. 2,713,593 (Brice et al.) and in R. E. Banks, Preparation, Properties and Industrial Applications of Organofluorine Compounds, pages 19-43, Halsted Press, New York (1982)), potassium fluoride (56.0 grams, 0.96 moles), diglyme (500 grams) and Adogen 464 (10.6 grams, 0.02 moles) were combined in 3 liter 3-neck round bottom flask equipped with overhead stirring, cold water condenser, dry nitrogen bubbler, heating mantle and thermocouple. An exothermic reaction increased the temperature to 30° C. When the temperature decreased to 25° C., dimethyl sulfate (107.4 grams, 0.85 moles) was added to the flask and the contents were heated to 32° C. and held six days. 350 mL of water and 200 grams of 50% potassium hydroxide were slowly added to the reaction mixture to quench the dimethyl sulfate and to start the decarboxylation reaction. The flask was heated to 65° C. and held two hours and then the mixture was distilled. The lower fluorochemical phase of the resulting distillate was then separated from the upper phase and washed twice with water to afford 360 grams of material. This material was purified by fractional distillation using a vacuum jacketed Oldersahw column to give 151.1 grams product (boiling range 150-151° C.), purity >95% by gas-liquid chromatography). The product identity as a mixture of cis and trans isomers was confirmed by GCMS.

Other embodiments of the invention are within the scope of the appended claims.

The invention claimed is:
1. A hydrofluoroether compound of the following general formula (I)

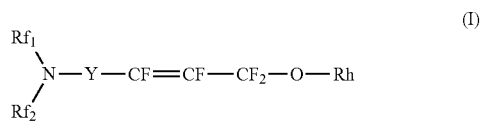

wherein (i) $Rf_1$ and $Rf_2$ are independently linear or branched perfluoroalkyl groups having with 1-8 carbon atoms and optionally comprise at least one catenated heteroatom, or (ii) $Rf_1$ and $Rf_2$ are bonded together to form a ring structure having 4-6 carbon atoms and optionally comprise one or more catenated heteroatoms;

wherein Y is $CF_2$ or a single bond; and wherein Rh is a linear or a branched alkyl group having with 1-3 carbon atoms and optionally comprises at least one catenated heteroatom;

with the proviso that if $Rf_1$ and $Rf_2$ are bonded together to form a ring structure comprising a nitrogen heteroatom, said nitrogen heteroatom is tertiary and is bonded to a perfluoroalkyl group having 1-3 carbon atoms.

2. The hydrofluoroether compound of claim 1, wherein $Rf_1$ and $Rf_2$ are bonded together to form a ring structure having 4-6 carbon atoms and optionally comprise one or more catenated heteroatoms.

3. The hydrofluoroether compound of claim 1, wherein $Rf_1$ and $Rf_2$ are independently linear or branched perfluoroalkyl groups having with 1-8 carbon atoms and optionally comprise at least one catenated heteroatom.

4. The hydrofluoroether compound of claim 1, wherein $Rf_1$ and $Rf_2$ are independently linear or branched perfluoroalkyl groups having 2-4 carbon atoms and optionally comprise at least one catenated heteroatom.

5. The hydrofluoroether compound according to claim 1, wherein Rh has 1-2 carbon atoms.

6. The hydrofluoroether compound of claim 1, wherein said compound is selected from the group consisting of:

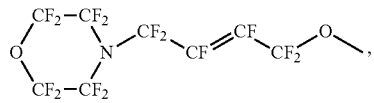

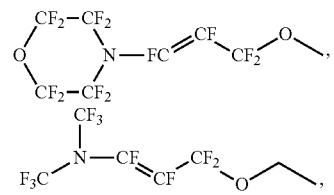

-continued

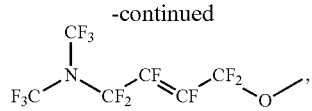

and combinations thereof.

7. A process for transferring heat comprising transferring heat between a heat source and a heat sink through the use of a heat transfer agent comprising a hydrofluoroether compound according to claim 1.

8. A process for depositing a coating on a substrate, the process comprising applying to at least a portion of at least one surface of said substrate a composition comprising (a) a solvent composition comprising a hydrofluoroether compound according to claim 1; and (b) at least one coating material that is soluble or dispersible in said solvent composition.

9. A process for removing a contaminant from an article, the process comprising contacting the article with a hydrofluoroether compound according to claim 1.

* * * * *